United States Patent [19]
Hayes et al.

[11] 4,444,747
[45] Apr. 24, 1984

[54] EXTRUDABLE DENTAL CREAM

[75] Inventors: Harry Hayes, Thelwall; Anthony J. Morton, Ashton-Under-Lyne; Kenneth Harvey, Wilmslow, all of England

[73] Assignee: Colgate-Palmolive Company, New York, N.Y.

[21] Appl. No.: 479,528

[22] Filed: Mar. 28, 1983

[51] Int. Cl.³ .......................... A61K 7/16; A61K 7/18
[52] U.S. Cl. ........................................ 424/52; 424/49
[58] Field of Search ...................................... 424/49–58

[56] References Cited
U.S. PATENT DOCUMENTS

| | | | |
|---|---|---|---|
| 3,070,510 | 12/1962 | Cooley et al. | 424/52 |
| 3,337,412 | 8/1967 | Elbreder | 424/151 |
| 3,903,252 | 9/1975 | Stearns et al. | 424/49 |
| 3,946,108 | 3/1976 | Tomlinson et al. | 424/49 |
| 4,020,154 | 4/1977 | Perla et al. | 424/49 |
| 4,022,881 | 5/1977 | Hawkins | 424/49 |
| 4,132,771 | 1/1979 | Schreiber et al. | 424/52 |
| 4,251,507 | 2/1981 | Olson | 424/49 |
| 4,344,931 | 8/1982 | Aguilar | 424/52 |

*Primary Examiner*—Shep K. Rose
*Attorney, Agent, or Firm*—Robert L. Stone; Murray M. Grill; Herbert S. Sylvester

[57] ABSTRACT

A dental cream of desirable rheological properties containing a hydrated alumina polishing material and high viscosity hydroxyethyl cellulose gelling agent.

8 Claims, No Drawings

EXTRUDABLE DENTAL CREAM

Sodium carboxymethyl cellulose has commonly been used as the gelling agent of commercial choice in dental cream in view of its availability and the generally satisfactory rheological properties it gives to dental creams. However, it does tend to cause dental creams to increasingly thicken with the passage of time.

Hydroxyethyl cellulose has been suggested as an alternative gelling agent to sodium carboxymethyl cellulose and indeed grades of hydroxyethyl cellulose such as Natrosol M have been used in commercial dental creams and grades have been set forth, for instance in U.S. Pat. No. 3,862,307 (Natrosol G), and U.S. Pat. No. 3,070,510 (viscosity of 75–125 cps-Brookfield; 20° C.; 2% in water) and U.S. Pat. No. 4,022,881 (Natrosol 250 H). Low viscosity grades of hydroxyethyl cellulose as described in U.S. Pat. Nos. 3,862,207 and 3,070,510, while generally satisfactory may tend to cause dental creams to undergo extensional rheology by forming a visible "tail" during container filling and upon extrusion onto a toothbrush.

In U.S. Pat. No. 4,022,881 a toothpaste was described containing as the thickening agent 5–30% of high viscosity hydroxyethyl cellulose (i.e. Natrosol 250 H) and 70–95% sodium carboxymethyl cellulose to avoid forming a toothpaste with a "stringy" texture, which would occur if the hydroxyethyl cellulose were used in above 30% of the thickening agent. Various "abrasives" including "calcium phosphates" are mentioned as "typical toothpaste abrasives". However, except for calcium carbonate, none are actually set forth in toothpaste. In view of the disclosure of this patent, it would not be expected that dental creams containing polishing agent consisting essentially of a calcium phosphate with a gelling agent consisting essentially of high viscosity hydroxyethyl cellulose would have desirable rheological properties such as lack of string (tail) formation. A non-stringy toothpaste containing calcium carbonate abrasive with a thickening agent mixture of 10% hydroxyethyl cellulose and 90% sodium carboxymethyl cellulose was also set forth.

In copending commonly assigned application U.S. Ser. No. 417,941 filed Sept. 14, 1982, by Anthony John Morton and Kenneth Harvey, dental cream is described in which there is little susceptibility to roughness upon ageing together with other desirable rheological properties such as good "stand up", absence of formation of a "tail" on an extruded ribbon of dental cream and good ribbon gloss. That dental cream contains a gelling agent mixture of sodium carboxymethyl cellulose and hydroxyethyl cellulose, each being present in a weight ratio of about 3:2 to 2:3.

In accordance with the present invention a gelling agent is employed which has desirable rheological properties such as absence of formation of a "tail" on an extruded ribbon of dental cream, other excellent extrudibility properties and good ribbon gloss, particularly when filled in or extruded from a dental cream tube or pressure differential (e.g. aerosol or vacuum) or mechanically operated dispensing container.

With further regard to prior art U.S. Pat. No. 4,022,881, a toothpaste was described containing as the thickening agent 5–30% of high viscosity hydroxyethyl cellulose (i.e. Natrosol 250 H) and 70–95% sodium carboxymethyl cellulose to avoid forming a toothpaste with a "stringy" texture, which would occur if the hydroxyethyl cellulose were used in above 30% of the thickening agent. Various polishing agents including "types of alumina" are mentioned as "typical toothpaste abrasives". However, except for calcium carbonate, none are actually set forth in toothpaste. In view of the disclosure of this patent it would not be expected that dental creams containing hydrated alumina polishing agent and high viscosity hydroxyethyl cellulose would not be "stringy" or tend to "tail".

It is an advantage of this invention that a gelling agent is provided for a dental cream which has desirable rheological properties.

It is a particular advantage of the invention that dental cream tailing is avoided and rheometry is improved even when hydroxyethyl cellulose is the only gelling agent, particularly when the dental cream is filled into and extruded from a pressure differential or mechanically operated container or a dental cream tube.

Other advantages will be apparent from consideration of the following specification.

In accordance with certain of its aspects, this invention relates to a dental cream comprising about 20–75% of a polishing material, at least about half of which is hydrated alumina and a dental vehicle comprising about 20–80% by weight based on the weight of the dental cream of a liquid phase containing water, humectant or mixture thereof and about 0.5–5% by weight based on the weight of the dental cream of a gelling agent consisting essentially of hydroxyethyl cellulose having a viscosity in a range the average of which is at least about 24,000 cps, determined on a Brookfield viscometer at 20° C., in a water:glycerine (1:1.56) solution with a No. 6 spindle at 20 rpm.

The gelling agent is present in the dental cream in amount of about 0.5–5% by weight, preferably about 0.8–2%, and most preferably about 0.9–1.4%. A grade of hydroxyethyl cellulose effective in the practice of the present invention is Tylose H1000P, available from Farbwerke Hoechst of Frankfurt am Main, Germany.

Tylose H 10000 P and other grades of hydroxyethyl cellulose in accordance with the present invention have viscosities in a range the average of which is at least about 24,000 cps. In the present specification viscosity values are determined on a Brookfield viscometer at 20° C., in a water:glycerine (1:1.56) solution with a No. 6 spindle at 20 rpm.

Hydroxyethyl cellulose grades which may be used in the present invention are set forth in the following table:

TABLE

| SUPPLIER | HEC GRADE | VISCOSITY |
| --- | --- | --- |
| Hercules | Natrosol 250 HR and 250 H | 17000–31000 |
|  | Natrosol 250 HHR and 250 HH | 37000–41000 |
| Hoechst | Tylose H 10000P | 20000–30000 |

Hydroxyethyl cellulose grades of viscosity not reaching an average of about 24,000 cps, such as Hercules 250 M and MR (average viscosity of 15,500 cps) and Hoechst Tylose H4000P (viscosity of up to 23,000 cps), do not provide the desired rheology when used as the only gelling agent.

In the dental cream formulation the dental vehicle comprises a liquid phase proportioned with the gelling agents to form an extrudible creamy mass of desirable consistency. In general, liquids in the dental cream will comprise chiefly water, glycerin, sorbitol, polyethylene glycol 400, propylene glycol, or the like including suitable mixtures thereof. It is advantageous usually to use a mixture of both water and a humectant or binder such as glycerine or sorbitol; typically about 10–30% by weight of water and about 15–50% by weight of humectant. It is preferred to use glycerine or sorbitol. The total liquid content will generally be about 20–80% by weight of the formulation.

The dental cream contains about 20–75% by weight of a polishing agent at least about half of which is hydrated alumina. If desired, up to about half of the total polishing agent may be additional dentally acceptable polishing material such as silica, dicalcium phosphate, calcined alumina, zirconium silicate, insoluble sodium metaphosphate etc. Preferably about 40–55% of polishing material, typically all hydrated alumina, is present.

The hydrated alumina employed in accordance with the instant invention is preferably small in particle size, i.e. at least about 85% of the particles are smaller than 20 microns, such as that classified as gibbsite (alpha alumina trihydrate) and normally represented chemically as $Al_2O_3 \cdot 3H_2O$ or $Al(OH)_3$.

The alpha alumina trihydrate may have a size in the range of about 2.6–10 microns. The alpha alumina trihydrate sold by Alcoa as C333 is a fine grade of gibbsite and is particularly highly desirable. The average particle size of C333 alumina is about 7–9 microns (Coulter-Counter). It is obtained by fine grinding of the grade of alumina trihydrate sold by Alcoa as C33. Other grades of hydrated alumina which may be employed include AF 260 and AF 230 sold by British Aluminium Company and SH 100 sold by Rhone-Poulenc.

The dental cream is typically packaged in a container form from which it can be readily extruded such as a pressure differential or mechanically operated dental cream dispenser or a lined or unlined aluminium tube or lead tube or laminated tube. The rheological properties are particularly desirable when a mechanically operated dispensing container of the type described in British Patent Application No. 2,070,695A, published Sept. 9, 1981, is employed. This dispensing container comprises a dispensing mouthpiece, a tension member, a piston and operating hand control. The disclosure of this published application is incorporated herein by reference. Pressure differential dispensing container may be of the aerosol or vacuum type.

The dental cream may contain a compound which provides at least about 100 ppm, of fluoride, typically about 100–10,000 ppm, typically about 750–2000 ppm. Compounds which provide fluorine include sodium fluoride, stannous fluoride, potassium fluoride, potassium stannous fluoride, sodium hexafluorostannate, stannous chlorofluoride, sodium monofluorophosphate and amine fluorides including mixtures thereof. Most typically in accordance with the present invention sodium monofluorophosphate or a mixture of sodium monofluorophosphate and sodium fluoride may be employed.

The dental cream may preferably contain sodium monofluorophosphate or a mixture of sodium monofluorophosphate and sodium fluoride in amount to provide about 100–10,000 ppm of fluorine, e.g. about 750–2000 ppm, of particularly about 1400–2000 ppm such as about 1400–1670 ppm. A binary fluoride system of sodium monofluorophosphate and sodium fluoride is desirably used in which about 30–40% of the fluorine (e.g. about 30–35%) is provided by sodium fluoride.

Sodium monofluorophosphate, $Na_2PO_3F$, as commercially available, may vary considerably in purity. It may be used in any suitable purity provided that any impurities do not substantially adversely affect the desired properties. In general, the purity is desirably at least 80%. For best results, it should be at least 85%, and preferably at least 90% by weight of sodium monofluorophosphate with the balance being primarily impurities or by-products of manufacture such as sodium fluoride and water-soluble sodium phosphate salt. Expressed in another way, the sodium monofluorophosphate employed should have a total fluoride content of above 12%, preferably above 12.7%, a content of not more then 1.5%, preferably not more than 1.2% of free sodium fluoride; and a sodium monofluorophosphate content of at least 12%; preferably at least 12.1% all calculated as fluoride.

As indicated above, sodium fluoride in the binary mixture is a separate fluorine-containing component from sodium monofluorophosphate. About 225–800 ppm of fluorine is preferably provided to the dental cream by sodium fluoride.

Any suitable surface active or detersive material may be included in the dentifrice compositions. Such compatible materials are desirable to provide additional detersive, foaming and anti-bacterial properties depending upon the specific type of surface active material and are selected similarly. These detergents are water-soluble compounds usually, and may be anionic, nonionic, or cationic in structure. It is usually preferred to use the water-soluble non-soap or synthetic organic detergents. Suitable detersive materials are known and include, for example, the water-soluble salts of higher fatty acid monoglyceride monosulphate detergent (e.g., sodium coconut fatty acid monoglyceride monosulphate), higher alkyl sulphate (e.g. sodium lauryl sulphate), alkyl aryl sulphonate (e.g. sodium dodecyl benzene sulphonate, higher fatty acid esters of 1,2-dihydroxy propane sulphonate) and the like.

Further surface active agents include the substantially saturated higher aliphatic acyl amides of lower aliphatic amino carboxylic acid compounds, such as those having 12 to 16 carbons in the acyl radical. The amino acid portion is derived generally from the lower aliphatic saturated monoaminocarboxylic acids having about 2 to 6 carbons, usually the monocarboxylic acid compounds. Suitable compounds are the fatty acid amides of glycine, sarcosine, alanine, 3-aminopropanoic acid and valine having about 12 to 16 carbons in the acyl group. It is preferred to use the N-lauroyl, myristoyl and palmitoyl sarcoside compounds, however, for optimum effects.

The amide compounds may be employed in the form of the free acid or preferably as the water-soluble salts thereof, such as the alkali metal, ammonium, amine and alkylolamine salts. Specific examples thereof are the sodium and potassium N-lauroyl, myristoyl and palmitoyl sarcosides, ammonium and ethanolamine N-lauroyl glycide and alanine. For convenience herein, reference to "amino carboxylic acid compound", "sarcoside", and the like refers to such compounds have a free carboxylic group or the water-soluble carboxylate salts.

Such materials are utilized in pure or substantially pure form. They should be as free as practicable from soap or similar higher fatty acid material which tends to reduce the activity of these compounds. In usual practice, the amount of such higher fatty acid material is less than 15% by weight of the amide and insufficient to substantially adversely affect it, and preferably less than about 10% of said amide material.

Various other materials may be incorporated in the dental creams of this invention. Examples thereof are colouring or whitening agents, preservatives, such as methyl p-hydroxybenzoate, astringent materials such as allantoin, zinc sulphate, and aluminium sulphate, stabilisers, pyridyl carbinol, tetrasodium pyrophosphate, silicones, chlorophyll compounds and ammoniated materials such as urea, diammonium phosphate and mixtures thereof. These adjuvants are incorporated in the instant compositions in amount which do not substantially adversely affect the desired properties and characteristics and are suitably selected and used in conventional amounts. Among the above mentioned materials, zinc sulphate and aluminium sulphate are effective to further reduce extensional rheology when present in amount of about 0.05–1.5% by weight.

For some purposes it may be desirable to include antibacterial agents in the compositions of the present invention. Typical antibacterial agents which may be used in amounts of about 0.01% to about 5%, preferably about 0.05% to about 1.0%, by weight of the dentifrice composition include:

$N^1$-4(chlorobenzyl)-$N^5$-(2,4-dichlorobenzyl)biguanide;
p-chlorophenyl biguanide;
4-chlorobenzhydryl biguanide;
4-chlorobenzhydrylguanylurea;
N-3-lauroxypropyl-$N^5$-p-chlorobenzylbiguanide;
1,6-di-p-chlorophenylbiguanidehexane;
1-(lauryldimethylammonium)-8-(p-chlorobenzyldimethylammonium)octane dichloride;
5,6-dichloro-2-guanidinobenzimidazole;
$N^1$-p-chlorophenyl-$N^5$-laurylbiguanide;
5-amino-1,3-bis(2-ethylhexyl)-5-methylhexahydropyrimidine;
and their non-toxic acid addition salts.

Any suitable flavouring or sweetening materials may be employed in formulating a flavour for the compositions of the present invention. Examples of suitable flavouring constituents include the flavouring oils, e.g., oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cyclamate, sodium saccharine dipeptides of U.S. Pat. No. 3,939,261 and oxathiazin salts of U.S. Pat. No. 3,932,606. Suitable flavour and sweetening agent may together comprise from about 0.01 to 5% or more of the composition.

The dental creams should have a pH practicable for use. A pH range of 3 to 10.5 is particularly desirable. The reference to the pH is meant to be the pH determination directly on the dental cream. If desired, materials such as benzoic, phosphoric or citric acid may be added to adjust the pH to, say 4 to 7.5.

The following example is further illustrative of the nature of the present invention, but it is to be understood that the invention is not limited thereto. The compositions are prepared in the usual manner and all amounts of the various ingredients are by weight unless otherwise specified.

EXAMPLE

The following dental creams are prepared by conventional dental cream formulation technique. Dental creams A and B are filled into the mechanical dispenser described in published British Patent application No. 2,070,695A. Dental cream C is filled into an unlined aluminium dental cream tube and dental cream D is filled into a lined aluminium dental cream tube.

| | PARTS | | | |
|---|---|---|---|---|
| | A | B | C | D |
| Sorbitol (70% solution) | 23.000 | 23.000 | — | 23.000 |
| Glycerine | — | — | 20.20 | — |
| Hydroxyethyl cellulose (Hercules Natrosol 250M) | — | 1.00 | — | — |
| Hydroxyethyl cellulose (Hoechst Tylose H10000P) | 1.00 | — | 1.30 | 1.00 |
| Alpha alumina trihydrate (Alcoa C333) | 52.000 | 52.000 | 52.00 | 52.000 |
| C12–C18 Alcohol Na sulphate (100% AI) | 0.5 | 0.5 | 1.5 | 1.5 |
| Zinc sulphate.7H$_2$0 | — | — | 0.48 | — |
| Aluminium sulphate.18H$_2$0 | — | — | — | 0.78 |
| Sodium saccharin | 0.17 | 0.17 | 0.20 | 0.17 |
| Methyl p-hydroxybenzoate | 0.08 | 0.08 | 0.08 | — |
| Sodium monofluorophosphate | 0.76 | 0.76 | — | — |
| Sodium fluoride | 0.10 | 0.10 | — | — |
| Pyridyl carbinol | 0.10 | 0.10 | — | — |
| Allantoin | 0.15 | 0.15 | 0.15 | — |
| Flavour | 1.20 | 1.20 | 1.00 | 1.20 |
| Phosphoric acid (85%) | 0.14 | 0.14 | | |
| Deionized water | q.s. to 100 | q.s to 100 | q.s. to 100 | q.s. to 100 |

During filling and upon extrusion the surfaces of the dental creams A, C and D are smooth and rheologically desirable while dental cream B undergoes extensional rheology during filling and upon extrusion from its container. Similar rheological effects to those exhibited by dental creams A, C and D occur when Tylose H10000P of dental creams A, C and D is replaced by Natrosol 250 H and Natrosol 250 HH. Tailing occurs when dental cream B (with Natrosol 250M) is filled into a dental cream tube.

Although the invention has been described with regard to a specific example and certain variations thereof, it will be apparent to one skilled in the art that various modifications may be made thereto which fall within its scope.

We claim:

1. A dental cream which is smooth and free from extensional rheology during filling and upon extrusion including absence of formation of a tail comprising about 20–75% by weight of a polishing material, at least about half of which is hydrated alumina and about 20–80% by weight based on the weight of the dental cream of a liquid phase containing water, humectant or mixture thereof and about 0.5–5% by weight based on the weight of the dental cream of a gelling agent consisting essentially of hydroxyethyl cellulose having a viscosity in a range the average of which is at least about 24000 cps, determined on a Brookfield viscometer in 2% by weight water:glycerine (1:1.56) solution at 20° C. with a No. 6 spindle at 20 rpm.

2. The dental cream claimed in claim 1 wherein about 40–55% of alpha-alumina trihydrate polishing agent is present.

3. The dental cream claimed in claim 1 wherein said hydroxyethyl cellulose is a grade having a viscosity of about 17,000–31,000; about 37,000–41,000; or about 20,000–30,000.

4. The dental cream claimed in claim 3 wherein said hydroxyethyl cellulose has a viscosity of about 20,000–30,000.

5. The dental cream claimed in claim 1 wherein fluorine-providing compound is present in amount which provides about 100–10,000 ppm of fluorine.

6. The dental cream claimed in claim 5 wherein said fluorine is provided by sodium monofluorophosphate in amount of about 750–2000 ppm.

7. The dental cream claimed in claim 5 wherein said fluorine about 750–2000 ppm of fluorine is provided by a binary fluoride system of sodium monofluorophosphate and sodium fluoride in which about 30–40% by weight of the fluorine is provided by sodium fluoride.

8. The dental cream claimed in claim 1 wherein zinc sulphate or aluminium sulphate is present in amount of about 0.05–1.5% by weight.

* * * * *